(12) United States Patent
Bhattacharyya et al.

(10) Patent No.: US 9,844,230 B2
(45) Date of Patent: *Dec. 19, 2017

(54) MOLECULARLY IMPRINTED POLYMERS SELECTIVE FOR NITROSAMINES AND METHODS OF USING THE SAME

(71) Applicant: British American Tobacco (Investments) Limited, London (GB)

(72) Inventors: Sumita Bhattacharyya, Lund (SE); Kevin McAdam, Southampton (GB); Anthony Rees, Furulund (SE); Börje Sellergren, Schwerte (DE); Christine Widstrand, Lund (SE)

(73) Assignee: BRITISH AMERICAN TOBACCO (INVESTMENTS) LTD, London (GB)

( * ) Notice: Subject to any disclaimer, the term of this patent is extended or adjusted under 35 U.S.C. 154(b) by 12 days.

This patent is subject to a terminal disclaimer.

(21) Appl. No.: 14/327,509

(22) Filed: Jul. 9, 2014

(65) Prior Publication Data

US 2014/0332015 A1 Nov. 13, 2014

Related U.S. Application Data

(63) Continuation of application No. 11/604,003, filed on Nov. 21, 2006, now Pat. No. 8,807,142, which is a (Continued)

(51) Int. Cl.
*A24B 15/22* (2006.01)
*A24B 15/24* (2006.01)
(Continued)

(52) U.S. Cl.
CPC ............ *A24B 15/245* (2013.01); *A24B 15/24* (2013.01); *A24D 3/02* (2013.01); *A24D 3/067* (2013.01);
(Continued)

(58) Field of Classification Search
None
See application file for complete search history.

(56) References Cited

U.S. PATENT DOCUMENTS 5,587,273 A 12/1996 Yan et al.
5,601,097 A 2/1997 De Grandpre et al.
(Continued)

FOREIGN PATENT DOCUMENTS

CA 2565129 A1 12/2005
EP 1756023 B1 4/2012
(Continued)

OTHER PUBLICATIONS

Analytical Letters, vol. 36, No. 8, pp. 1631-1645, 2003.*
(Continued)

*Primary Examiner* — Michael H Wilson
*Assistant Examiner* — Phu Nguyen
(74) *Attorney, Agent, or Firm* — Cantor Colburn LLP

(57) ABSTRACT

A class of molecularly imprinted polymers that specifically recognizes and binds to nitrosamines members of which class are useful, for example, in analysis and separation of nitrosamines from biological fluids. Such molecularly imprinted polymers are also useful in methods of treating and manufacturing tobacco products and materials.

12 Claims, 7 Drawing Sheets

Related U.S. Application Data continuation of application No. PCT/SE2005/000773, filed on May 24, 2005.

(60) Provisional application No. 60/573,337, filed on May 24, 2004.

(51) Int. Cl.

| | |
|---|---|
| A24D 3/08 | (2006.01) |
| B01J 20/26 | (2006.01) |
| B01D 15/38 | (2006.01) |
| A24D 3/02 | (2006.01) |
| A24D 3/06 | (2006.01) |
| C08F 222/14 | (2006.01) |
| G01N 33/00 | (2006.01) |

(52) U.S. Cl.
CPC ............ *A24D 3/08* (2013.01); *B01D 15/3852* (2013.01); *B01J 20/268* (2013.01); *C08F 222/14* (2013.01); *G01N 33/0098* (2013.01)

(56) References Cited

U.S. PATENT DOCUMENTS

| | | | | |
|---|---|---|---|---|
| 5,810,020 | A * | 9/1998 | Northway et al. | ............ 131/297 |
| 8,252,876 | B2 | 8/2012 | Yilmaz et al. | |
| 8,733,369 | B2 * | 5/2014 | Rees | ............ A24B 15/245 131/290 |
| 8,807,142 | B2 * | 8/2014 | Bhattacharyya | ....... A24B 15/24 131/297 |
| 8,889,795 | B2 * | 11/2014 | Rees | ............ A24B 15/245 525/279 |
| 9,169,341 | B2 * | 10/2015 | Rees | ............ A24B 15/245 |
| 2002/0134394 | A1 * | 9/2002 | Baskevitch et al. | ......... 131/297 |
| 2003/0003587 | A1 | 1/2003 | Murray | |
| 2007/0186940 | A1 | 8/2007 | Bhattacharyya et al. | |
| 2013/0139834 | A1 | 6/2013 | Karlsson et al. | |
| 2013/0139835 | A1 | 6/2013 | Karlsson et al. | |
| 2015/0038648 | A1 | 2/2015 | Rees et al. | |

FOREIGN PATENT DOCUMENTS

| | | |
|---|---|---|
| WO | 9411403 | 5/1994 |
| WO | 9933768 | 7/1999 |
| WO | 0032648 | 6/2000 |
| WO | 0165954 A1 | 9/2001 |
| WO | 2005112670 | 12/2005 |
| WO | 2006/067431 A1 | 6/2006 |

OTHER PUBLICATIONS

Dirion et al. Chromatographia 2002, 56 August (No. 3-4).*
Sellergren et al., "Highly Enantioselective and Substrate-Selective POlymers Obtained by Molecular Imprinting Utilizing Noncovalent Interactions, NMR and Chromatographic Studies on the Nature of Recognition," J. Am. Chem. Soc. 1988, 110:5853-5860. [Previously submitted to USPTO in U.S. Appl. No. 11/604,003, filed Nov. 21, 2006.].
Liu et al., "Molecularly Imprinted Solid-Phase Extraction Sorbent for Removal of Nicotine from Tobacco Smoke," Analytical Letters, 2003, 36(8):1631-1645.
Zander et al., "Analysis of Nicotine and Its Oxidation Products in Nicotine Chewing Gum by a Molecularly Imprinted Solid-Phase Extraction," Anal. Chem. 1998, 70:3304-3314.
International Search Report, dated Aug. 29, 2005, for International Patent Application No. PCT/SE2005/000773, filed May 24, 2005. [Previously submitted to USPTO in U.S. Appl. No. 11/604,003, filed Nov. 21, 2006.].
Sellergren, B. and Esteban, A.M., "The Use of Molecularly Imprinted Polymers for Sampling and Sample Preparation," Chapter 23, Handbook of Sample Preparation (2011), pp. 443-471. [Previously submitted to USPTO in U.S. Appl. No. 11/604,003, filed Nov. 21, 2006.].
Cook, A., et al., "Basicity of Some Mono- and Bicyclic Enamines and Tricyclenamines," J. Org. Chem., 1995, 60, 3169-3171. [Previously submitted to USPTO in U.S. Appl. No. 11/604,003, filed Nov. 21, 2006.].
International Preliminary Report on Patentability dated Sep. 4, 2006 for International Patent Application No. PCT/SE2005/000773, filed May 24, 2005. [Previously submitted to USPTO in U.S. Appl. No. 11/604,003, filed Nov. 21, 2006.].
Liqing Wu et al., "Study on the recognition of templates and their analogues on molecularly imprinted polymer using computational and conformational analysis approaches," 2004 (17) pp. 567-574. [Previously submitted to USPTO in U.S. Appl. No. 11/604,003, filed Nov. 21, 2006.].
Jun Matsui, et al. "A Molecularly Imprinted Nicotine-Selective Polymer." Analytical Letters, 1996, pp. 2071-2078. [Previously submitted to USPTO in U.S. Appl. No. 11/604,003, filed Nov. 21, 2006.].
Borje Sellergren, Molecularly Imprinted Polymers, First Edition 2001, Elsevier Science B.V. [Physical Book—Previously submitted to USPTO in U.S. Appl. No. 11/604,003, filed Nov. 21, 2006.].
Dirion et al., Selective Solid Phase Extraction of a Drug Lead Compound Using Molecularly Imprinted Polymers Prepared by the Target Analogue Approach, 2002, Chromatographia, 56, August (No. 3/4) [Provided by Examiner in U.S. Appl. No. 11/604,003, filed Nov. 21, 2006.].
"Enamine Chemistry IV. Cyloaddition Reaction of Enamines Derived from Aldehydes and Acyclic Ketones" by Brannock et al., Apr. 1964. [Previously submitted to USPTO in U.S. Appl. No. 11/604,003, filed Nov. 21, 2006.].
"Liquid chromotographic/tandem mass spectrometric method for the determination of the tobacco-specific nitrosamine metabolite NNAL in smokers' urine" by Byrd et al., 2003 [Previously submitted to USPTO in U.S. Appl. No. 11/604,003, filed Nov. 21, 2006.].
"Review of Molecular Imprinting Used for Chiral Separations" by Kempe et al., 1995. [Previously submitted to USPTO in U.S. Appl. No. 11/604,003, filed Nov. 21, 2006.].
"Molecularly Imprinted Solid-Phase Extraction Sorbent for Removal of Nicotine from Tobacco Smoke" by Liu et al., 2003. [Previously submitted to USPTO in U.S. Appl. No. 11/604,003, filed Nov. 21, 2006.].
"Molecularly imprinted polymers: useful materials for analytical chemistry?" by Mayes et al., 1997. [Previously submitted to USPTO in U.S. Appl. No. 11/604,003, filed Nov. 21, 2006.].
"Noncovalent molecular imprinting: antibody-like molecular recognition in polymeric network material" by Sellergren, 1997. [Previously submitted to USPTO in U.S. Appl. No. 11/604,003, filed Nov. 21, 2006.].
"Simultaneous Determination of Five Tobacco-Specific Nitrosamines in Mainstream Cigarette Smoke by Isotope Dilution Liquid Chromatography/Electrospray Ionization Tandem Mass Spectrometry" by Wu et al., 2003. [Previously submitted to USPTO in U.S. Appl. No. 11/604,003, filed Nov. 21, 2006.].
"Molecular Imprinting in Cross-Linked Materials with the Aid of Molecular Templates—A Way Towards Artificial Antibodies" by Wulff, 1995. [Previously submitted to USPTO in U.S. Appl. No. 11/604,003, filed Nov. 21, 2006.].
Communication from the EPO Examining Division (with Annex), dated Sep. 21, 2009, for corresponding European Patent Application No. 05744145.3, filed May 24, 2005.
Decision to Grant a European Patent, dated Mar. 15, 2012, for corresponding European Patent Application No. 05744145.3, filed May 24, 2005.
Written Opinion, dated Jun. 19, 2006, for International Patent Application No. PCT/SE2005/000773, filed May 24, 2005.
Australian Office Action, dated Aug. 19, 2010, for Australian Patent Application No. 2007329060, filed Nov. 26, 2007.
International Search Report and Written Opinion, dated Jul. 25, 2008, for International Application No. PCT/EP2007/062781, filed Nov. 26, 2007.

(56) References Cited

OTHER PUBLICATIONS

International Preliminary Report on Patentability, dated Jun. 10, 2009, for International Application No. PCT/EP2007/062781, filed Nov. 26, 2007.

Notice of Acceptance from Australian Patent Office, dated May 9, 2011, for Australian Patent Application No. 2007329060, filed Nov. 26, 2007.

Xia Yang, et al., "Analysis of the tobacco-specific nitrosamine . . . " Anal. Chem., Amer. Chem. Soc., vol. 77, No. 23, Dec. 1, 2005, pp. 7639-45.

Masqué, N. et al. "Molecularly imprinted polymers: new tailor-made materials for selective solid-phase extraction", Trends in Analytical Chemistry, vol. 20, No. 9, 2001, pp. 477-486.

"SupelMIP Highly Selective SPE for Trace Analysis in Complex Matrixes," Sigma-Aldrich, 2006.

Shimelis, O.; Whilborg, A.; Aurand, C.; Trinh, A. "Trace Level Analysis of NNAL in Urine Using SupelMIP SPE-NNAL and LC-MS-MS." Supelco Reporter (International), 2007, 28, 7-10.— See more at: http://www.sigmaaldrich.com/technical-documents/articles/analytix/trace-analysis-of.html#sthash.yCo57nJc.dpuf.

Naghash, Hamid J. et al., "Size Distribution of Polymers During . . . ," Polymer Bulletin 37, pp. 207-213 (1996).

Okay, Oguz et al., "Synthesis and Formation Mechanism of Porous 2-Hydroxyethyl Methacrylate-Ethylene . . . ," Journal of Applied Polymer Science, vol. 46, 401-410 (1992).

Okay, O., "Macroporous Copolymer Networks," Prog. Polym. Sci. 25 (2000) pp. 711-779.

Vianna-Soares, Cristina D., et al., "HPMA and HEMA Copolymer Bead Interactions with Eukaryotic Cells," Materials Research, vol. 7, No. 3, 473-477, 2004.

\* cited by examiner

MOLECULARLY IMPRINTED POLYMERS SELECTIVE FOR NITROSAMINES AND METHODS OF USING THE SAME

CROSS-REFERENCE TO RELATED APPLICATIONS

This application is a continuation of U.S. patent application Ser. No. 11/604,003, filed Nov. 21, 2006, which is a continuation of international PCT application Serial No. PCT/SE2005/00773 filed May 24, 2005 and published as WO2005/112670 in English on Dec. 1, 2005, which claims priority under 35 U.S.C. §119 to U.S. provisional application Ser. No. 60/573,337 filed May 24, 2004. The entire contents of the aforementioned applications are herein expressly incorporated by reference.

FIELD OF THE INVENTION

The present invention relates to a class of molecularly imprinted polymers and use of the molecularly imprinted polymers in bioanalysis and separation of nicotine metabolites. The invention further relates to methods of using the molecularly imprinted polymers to treat tobacco, tobacco substitutes, and their derivatives to reduce the level of targeted compounds therein.

BACKGROUND OF THE INVENTION

In the fields of medical, dietary, environmental and chemical sciences there is an increasing need for the selective separation of specific substances from complex mixtures of related substances. The aim can be the quantitative extraction of a certain compound or compounds, the measurement of their concentration or the selective removal of a target compound from a multi-component mixture.

Stricter health controls have increased the demand for methods allowing sensitive and selective quantification of hazardous products and metabolites from certain everyday substances in widespread use. Of particular concern are chemical compounds related to use of tobacco-based products, which compounds are either originally present in the raw tobacco leaf itself or generated during the smoking process. Nitroso-containing compounds, such as nitrosamines, are regarded as being of special significance in this regard.

With the aim of reducing the occurrence of hazards related to smoking, certain pharmaceutical products have been produced containing only the neuroactive substance, nicotine, the chemical claimed to be responsible for the dependence aspects of smokable material.

Among the nicotine formulations for smoking cessation therapy, nicotine chewing gum has found the most widespread use. The quality control required during production includes monitoring of the nicotine level (2 or 4 mg per gum) as well as monitoring of the primary nicotine oxidation products cotinine, myosmine, nicotine-cis-N-oxide, nicotine-trans-N-oxide and beta-nicotyrine. Quantitation of nomicotine, anatabine and anabasine is also desirable, if not required. According to the United States Pharmacopeia (U.S.P.) the gum formulation should contain between 95% and 110% of the amount of nicotine given on the label and the amount of each oxidation product should not exceed 0.1% of the nicotine amount.

Despite the use of such cigarette substitutes, nitrosamine nicotine metabolites may be produced in vivo by natural metabolic processes during the residence of the nicotine within body tissues. The levels of these metabolites remain below the concentrations at which most analytical procedures can perform quantitatively. The need for methods which are capable of monitoring these levels, as well as the levels of other nicotine metabolites, is therefore of importance. Typically, such monitoring is performed on human urine samples in which levels of such suspected carcinogens are extremely low.

Targeted compounds for quantification, reduction or removal from tobacco or smoke are known and include the major components of tobacco-specific nitrosamines (TS-NAs) and their alkaloid precursors: NNK, 4-(methylnitrosamino)-1-(3-pyridyl)-1-butanone; NNA, 4-(methylnitrosamino)-4-(3-pyridyl)butanal; NNN, N-nitrosonomicotine; NAB, N-nitrosoanabasine; NAT, N-nitrosoanatabine; NNAL, 4-(methylnitrosamino)-1-(3-pyridyl)-1-butanol; iso-NNAL, 4-(methylnitrosamino)-4-(3-pyridyl)-1-butanol; iso-5 NNAC, 4-(methylnitrosamino)-4-(3-pyridyl)butanoic acid.

To properly quantify how much of such targeted compounds are present in human biological fluids, methods are being developed to analyse the alkaloids, especially the nitrosylated decomposition products and metabolites in tobacco. Existing chromatographic separation or extraction methods used for this analysis lack the robustness, sensitivity and speed required in order to handle the large number of samples generated when screening the general population. With existing methods, the low concentration of the nitrosamines, which are typically present in picograms per milliliter, demands extensive sample preparation with multi-step extractions and often chemical derivatization (for example deuteration prior to mass spectrometry) of the analyte prior to analysis. One reason for this complexity is that the existing separation materials are not selective as, for example, an antibody or biological receptor might be for the metabolites in question but rather rely on physico-chemical properties like charge or hydrophobicity of the metabolites for the separation behaviour. These physico-chemical properties may be shared by many other irrelevant molecules in the sample.

A typical procedure might involve up to seven work-up steps including centrifugations, pH adjustments, enzymatic treatments, etc., which may sum up to a preparation time of many hours or even days per sample. With such cumbersome procedures, loss of material during the process can lead to errors in estimation of the original sample concentrations, requiring extrapolation back from the final measurement, rather then reliance on direct measurement, to obtain the original concentration in the sample. A quick and simple method for the analysis of tobacco-specific nitrosamines is therefore a significant unmet medical analytical need. (See, e.g. Byrd & Ogden, Journal of Mass Spectrometry, 2003, 38, 98-107 and Wu et al. Anal. Chem. 2003, 75, 4827-4832).

During recent years numerous reports of selective recognition of small molecules with materials prepared by molecular imprinting (molecularly imprinted polymers or MIPs) have appeared. See, for example, Wulff, G. Angew, Chemie. Int. Ed. Engl. 1995 (34) 1812. MIPs are polymers having reactive sites adapted to bind selectively with targeted compounds. Non-covalently prepared molecularly imprinted materials have been used for chiral recognition of a variety of small molecules including therapeutic drugs, sugars, molecular bases, and pesticides as well as steroid and peptide hormones. Examples of the same are described in, for example, Sellergren, B. Trends Anal. Chem. 1997 (16) 310. The high affinity and selectively for the target analyte exhibited by some of the imprinted materials have justified a comparison with the corresponding immuno-affinity (IA) phases. In contrast to the latter phases however, the MIP materials are straightforward to prepare, stable in most media and reusable over long periods of time. Applications of the MIP materials in chromatography, separation (continuous or batch), chemical sensing or in specific assays are therefore under investigation.

Another application is solid-phase extraction (SPE, see Mayes, A. G., Mosbach, K. Trends Anal. Chem. 1997, 16, 321) of analytes present in low concentrations in biological samples, or in complex matrices. SPE may lead to selective enrichment and clean-up of an analyte to levels not achievable with existing methods. Molecularly imprinted solid phase extractions (MISPE) have been used in bioanalysis, food analysis and environmental analysis. In these examples selective enrichment and clean-up of the analyte is obtained resulting in higher accuracy and a lowering of the detection limit (LOD) in the subsequent chromatographic (eg HPLC) or mass spectrometric quantification.

In view of their high selectivity combines with good affinity for the target molecule or a group of target molecules, MIPs have attracted considerable interest from the food industry as a tool to improve food quality. This requires the use of a MIP for selective removal of undesirable components from the food matrix. Since these components are often present in low concentrations, the saturation capacity of the MIP is typically not a limiting factor.

The preferred specifically designed MIP material of the invention is capable of selectively absorbing the most common nitrosylated nicotine derivatives from complex matrices, such as urine, giving quantitative recovery and thereby leading to low errors in the estimation of such hazardous chemical concentrations.

In addition to quantifications it is also well known to attempt to reduce the harmful effects of consuming material containing tobacco, tobacco substitutes or mixtures thereof by reducing the levels of targeted compounds. Such reductions can be made in the material itself or in a derivative thereof such as an extract of the material. Reduction can also be effected in the thermal decomposition products of the material, i.e. mainstream and sidestream smoke obtained by combustion, or the aerosols produced by heating the material to a temperature below its combustion temperature.

One very well known method for this sort of reduction is to contact the thermal decomposition products of the material with a filter that adsorbs undesired components therefrom. An alternative method involves solvent extraction of the material, for example as disclosed in the specification of U.S. Pat. No. 5,601,097. According to that specification, the protein content of tobacco material is reduced by treating the tobacco with a solution containing a surfactant to extract polypeptides, separating the solution, removing the surfactant and the polypeptides from the solution, and recombining the solution with the tobacco material. International patent application specification WO 01/65954 discloses a process in which tobacco is contacted with a supercritical extraction fluid such as supercritical carbon dioxide to selectively reduce or eliminate nitrosamines.

These processes are equally applicable to both tobacco itself and to tobacco substitutes i.e. natural or synthetic materials having similar characteristics to natural tobacco that enable them to be consumed in a similar way to tobacco, whether by smoking, chewing, inhalation or otherwise.

There has been an attempt to remove nicotine from tobacco smoke using MIPs, as reported in Liu, Y., et al., Molecularly imprinted Solid-Phase Extraction Sorbent for Removal of Nicotine from Tobacco Smoke, Analytical Letters, Vol. 36, No. 8, pp 1631-1645 (2003). The MIP described in the article was designed to bind nicotine and not the more toxic nicotine metabolites such as nitrosamines. It is unclear if the MIP was in fact selective for nicotine as the scientific method producing the data was lacking in key control-checking elements.

Therefore, there remains a need in the art for novel MIPs and methods of employing the same, particularly in the field of nicotine and nicotine metabolites.

SUMMARY OF THE INVENTION

Broadly, the present invention provides a molecularly imprinted polymer (MIP) selective for nitroso-containing compounds.

The preferred MIPs of the invention are selective for nitrosamines, in particular TSNAs or the volatile nitrosamines found in the vapor phase of the thermal decomposition products of smoking materials. Another preferred MIP of the invention is selective for one or more of the nitrosylated derivatives of nicotine or the other alkaloids found in tobacco, namely nornicotine, anabasine and anatabine.

The MIPs of the invention can be obtained, for example, by co-polymerising a functional monomer, or monomers and a cross-linker in the presence of a structural analogue of a nitrosamine, in a polymerization medium containing a free radical initiator, after which the template is removed from the MIP.

The invention includes the use of the molecularly-imprinted polymers of the invention for analytical and preparative extractions, in chromatography, for analytical sample pre-treatment, in chemical sensors or as a solid phase filter for extraction of nicotine nitrosamines from nicotine-containing substances or devices.

Additionally, the invention includes a method of reducing the level of a targeted component in a tobacco product, in which the tobacco product is treated with a MIP which is selective for at least one nitroso-containing compound. Further, the invention provides methods of manufacturing a smoking material which incorporates use of MIPs to selectively remove nitroso-containing compounds.

The present invention includes the treatment of tobacco products with MIPs to reduce the level of nitroso-containing compounds therein.

In this specification, "tobacco product" means a material containing tobacco (including tobacco leaf or tobacco stem), or a tobacco substitute, or a blend of tobacco and tobacco substitutes, and derivatives of such material, including extracts of the material, smoke produced by thermal decomposition of the material and aerosols produced by heating the material to below its combustion temperature.

Where the tobacco product is a derivative produced by the thermal decomposition of material containing tobacco or a tobacco substitute, the decomposition may be effected by combustion of the material, as in a conventional cigarette, or by heating the material to a temperature below its combustion temperature, in accordance with a process used in some known alternative tobacco products in order to produce an aerosol that is inhaled by the consumer.

Alternatively, the tobacco product may be a derivative produced by contacting material containing tobacco or a tobacco substitute with a solvent. In particular, the invention provides a method of manufacturing a material for smoking comprising the steps of extracting smokable material with a solvent, treating the extract with a molecularly imprinted polymer selective for at least one nitroso-compound to reduce the level thereof in the extract and combining the treated extract with the smokable material.

In this process, the smokable material may be in any convenient form, for example fines, stems, scraps, cut lamina, shredded stems, or any combination thereof. The solvent may be aqueous or non-aqueous, such as methanol, ethanol or a super-critical fluid extraction medium, such as super-critical carbon dioxide liquid. The extraction may be carried out under any conditions favoring the extraction of nitrogen-containing compounds from tobacco.

The invention also includes a smoking article comprising tobacco or tobacco substitute, and a molecularly imprinted polymer selective for the removal of at least one nitroso-containing compound from the thermal decompositions product thereof.

The smoking article of the invention may take any conventional form, for example a cigarette, cigar or cigarillo. In particular the smoking article may comprise a rod of smoking material optionally in a wrapper, with or without a filter. The wrapper may be of paper, tobacco leaf, reconstituted tobacco or a tobacco substitute. Alternatively, where, for example, the smoking article is intended to produce low emissions of sidestream smoke, or lower levels of pyrolysis products in the mainstream smoke, the wrapper may be composed of non-combustible inorganic material such as a ceramic material. The filter may be of any suitable material, for example fibrous cellulose acetate, polypropylene or polyethylene, or paper.

The smoking material is preferably tobacco but may be a tobacco substitute such as non-tobacco smoking material. Examples of non-tobacco smoking materials are dried and cured vegetable material, including fruit materials, and a synthetic smoking material such as may be produced from alginates and an aerosol-generating substance such as glycerol. The smoking material may also comprise a blend of tobacco and non-tobacco smoking materials. Where the smoking material comprises tobacco, the tobacco may of any suitable type, or a blend thereof, including air-cured, fire-cured, flue-cured, or sun-cured lamina or stem, and may have been processed using any appropriate process. For example, the tobacco may be cut, shredded, expanded or reconstituted. The smoking material may also include conventional additives, such as ameliorants, colorants, humectants (such as glycerol and propylene glycol), inert fillers (such as chalk), and flavourings (such as sugar, liquorice and cocoa).

The invention may also be applied to tobacco that is intended for oral or nasal consumption by sucking, chewing, or nasal ingestion, rather than smoking. Such products include snuff, snus and "hard" or chewing tobacco.

The molecularly imprinted material may be incorporated is the smokable material. Accordingly, the invention includes smoking material containing a molecularly imprinted polymer selective for the removal of at least one nitroso-containing compound from the thermal decomposition products of the smokable material.

Alternatively, where the smoking article comprises a rod of smokable material is a wrapper, the molecularly imprinted material may be incorporated in the wrapper. The invention therefore includes wrapper material for smoking articles comprising a molecularly-imprinted, polymer selective for the removal of a targeted component from the thermal decomposition products of a smoking material. The wrapper may be a cellulose-based material such a paper or a tobacco based material such as reconstituted tobacco.

The preferred smoking articles of the invention are cigarettes, comprising a rod of tobacco, wrapper, and a filter including a molecularly imprinted polymer selective for the removal of at least one nitroso-containing compound from the thermal decomposition products of a smokable material.

The invention also includes a smoke filter comprising a molecularly imprinted polymer selective for the removal of at least one nitroso-containing compound from the thermal decomposition products of a smoking material. The smoke filter may be produced separately from the smoking article, for example in the form of a cigarette or cigar holder, or it may be integrated into the smoking article, for example in the form of a cigarette with a filler tip.

Smoke filters in the form of filter tips may be of any conventional construction. For example it may in the form of a "dalmation" type filter comprising a section of fibrous filter material, such as cellulose acetate, the molecularly imprinted polymer being in particular form and distributed throughout the section. Alternatively the filter may be in the form of a "cavity" type filter, comprising multiple sections wherein the molecularly imprinted polymer may lie between two adjacent sections of fibrous filter material. The smoke filter may also comprise other adsorbent materials such as an ion-exchange resin, a zeolite, silica, alumina or amberlite.

In use, the smoke passes through the filter, the molecularly imprinted polymer selectively adsorbs and retains the targeted compounds from the smoke and the filtered smoke is delivered to the smoker.

The smoke filters and smoking articles according to the invention may include means for protecting the molecularly imprinted polymer from, or reducing its exposure to, smoke when in use. This may be achieved in a number of different ways. For example the smoke filter may comprise a filter element for adsorbing materials from the vapor or particulate phase of smoke. Such filter elements may comprise a general adsorbent such as activated carbon, which may be in any convenient form, such as threads, particles, granules, cloth, or paper. The filter element may also be a selective adsorbant such as an ion-exchange resin, a zeolite, silica, alumina or amerlite. The means for protecting the catalyst may include two or more such filter element of different compositions, for example a first filter element of cellulose acetate, and a second filter element of activated carbon. The provision of multiple filter elements in smoke filters and smoking articles is well known, and any conventional configuration of filter, and associated methods of construction, may be used.

BRIEF DESCRIPTION OF THE DRAWINGS

In the drawings, similar features are gives like reference numerals.

DETAILED DESCRIPTION OF THE PREFERRED EMBODIMENTS

Figure 1:
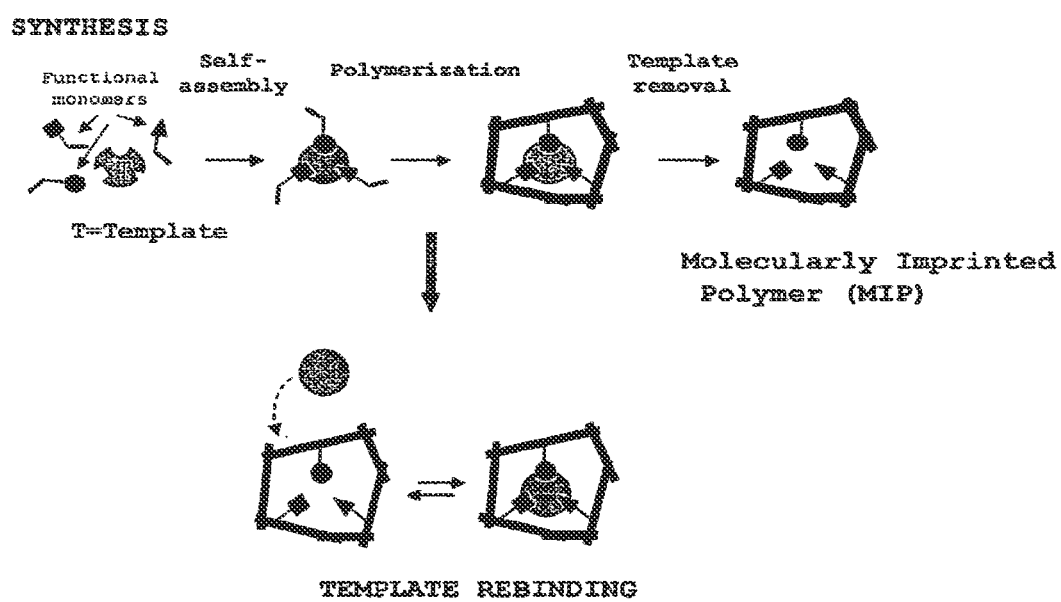
FIG. 1 shows an outline of the procedure for synthesis of an imprinted polymer.

Molecular imprinting typically consists of the following steps: (1) a template compound, which may be the targeted molecule or a structural analogue thereof, is allowed to interact with a selected functional monomer, or monomers, in solution to form a template-monomer complex; (2) the template-monomer complex is co-polymerized with a cross-linking monomer resulting in a polymeric matrix incorporating the template compound; (3) the template compound is extracted from the polymer matrix to form a MIP that can be used for selective binding of the targeted molecule. Prior to step (3), where the MIP is prepared as a solid polymer (or monolith) it is typically crushed and sieved to obtain a desired size fraction of particulate material. When prepared by either suspension or emulsion polymerization methods, such crushing and sieving is unnecessary since the particle size can be controlled within the desired limits during the polymerization process. Particulate material prepared by any of the aforementioned methods can be packed into a chromatographic or solid phase extraction column and used for chromatographic separation of the template from other components of a mixture, including molecules with similar structures or functionalities.

The reactive sites on the molecularly imprinted polymer exposed by removal of the template composed will be in a stereo-chemical configuration appropriate for reaction with fresh molecules of the targeted molecule. As a result, the polymer can be used for selective binding of the targeted molecule.

Currently the most widely applied technique to generate molecularly imprinted binding sites is via the 'non-covalent' roots. This makes use of non-covalent self-assembly of the template compound and functional monomers to form the template-monomer complex, followed by free radical polymerization in the preserve of a cross-linking monomer and finally template compound extraction. Covalent imprinting, in which the template molecule and a suitable monomer or monomers are covalently bound together prior to polymerization can also be carried out according to known methods. The birthing properties of the MIPs formed by either of the above methods can be examined by reminding of the template molecule.

The polymerization is performed in the presence of a pore-forming solvent called a porogen. In order to stabilize the electrostatic interactions between the functional momomers and the template compound the porogen is often chosen from among aprotic solvents of low to moderate polarity. Ideally, template compounds exhibit moderate to high solubility in the polymerization media and these, or their structural analogues, can therefore be used directly using this standard procedure.

While it is possible to use the targeted molecule itself as the template, a structural analog of the target molecule is commonly preferred because: (a) the targeted molecule may be unstable under the polymerization conditions or may inhibit the polymerization; (b) the targeted molecule may not be available in sufficient quantities due to complexity of its synthesis or cost, or both; (c) the template may be insoluble or poorly soluble in the pre-polymerization mixture; (d) the MIP may remain contaminated by low levels of the targeted molecule retained in poorly accessible regions of the polymer matrix, which may bleed from the MIP during use; and/or (e) the target analyte(s) may present a significant health risk and should not be used as a template(s).

Figure 2:
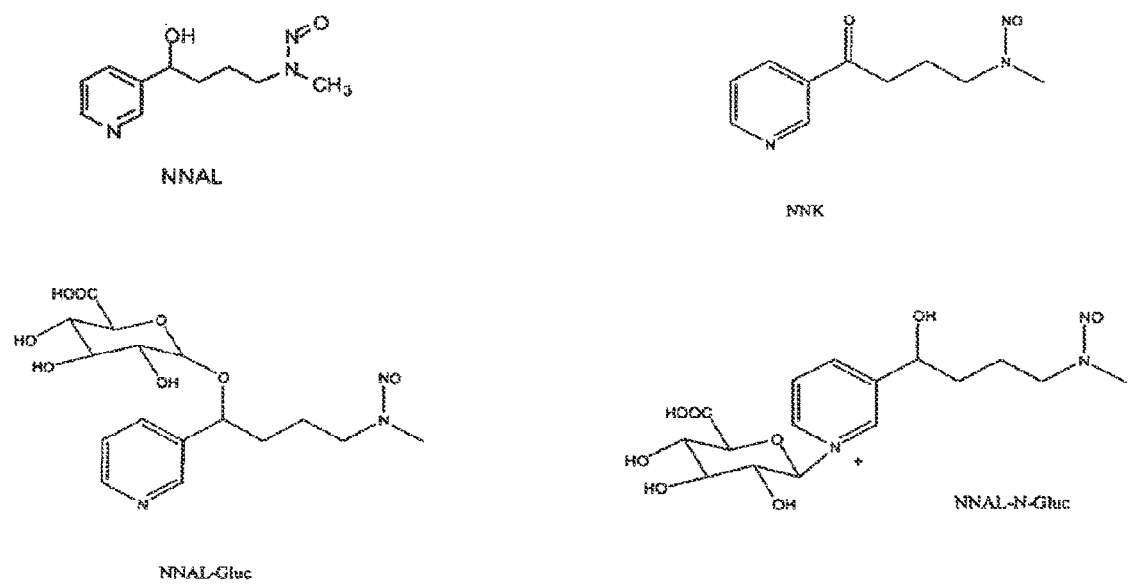
FIG. 2 shows the nitrosamine functional group and examples of nicotine related-nitrosamine targets.

In the case of nitroso-compounds, particularly the compounds known as TSNAs described below, it is often more convenient to use functional analogues thereof as template compounds. For example, glucose derivatives of TSNAs may be particularly useful as template compounds, see FIG. 2.

Where the MIP is derived using a functional analog of the targeted compound, the functional analogue should be isosteric and preferably also isoelectronic with the targeted compound, or it may contain a substructure of the targeted compound where strong interactions may be likely.

Nitroso-containing compounds, particularly nitrosamines, which have the general formula $O=N-N(R_1)(R_2)$ are among the numerous ingredients of tobacco and tobacco smoke that have been suggested as having a harmful effect on consumers.

One particular class of nitroso compounds to which the present invention is applicable is the group of nitrosamines that occur naturally in tobacco, known as tobacco-specific nitrosamines (TSNAs), which are derived from the alkaloids that occur naturally in tobacco namely nicotine, nornicotine, anabasine and anatabine. TSNAs include:

4-(methylnitrosamino)-1-(3-pyridyl)-1-butanone ("NNK"):

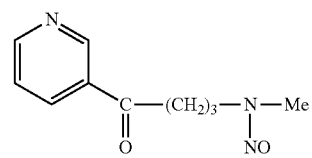

N'-nitrosonornicotine ("NNN"):

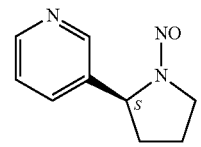

N'-nitrosoanabasine ("NAB"):

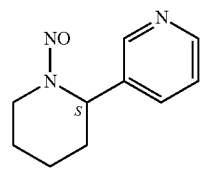

N'-nitrosoanatabine ("NAT"):

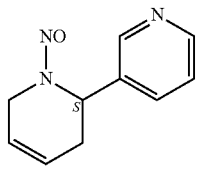

4-(methylnitrosamino)-4-(3-pyridyl)butanol ("NNA")

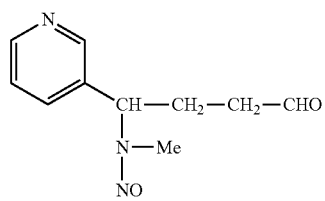

In addition, a group of compounds known as volatile nitrosoamines is found in the vapor phase of tobacco smoke. This group includes the following compounds:

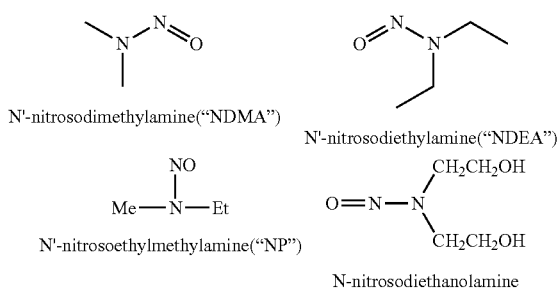

Other nitroso-containing compounds have also been identified in chemical studies of tobacco or tobacco smoke, for example:

N-nitrosopyrrolidine ("NYPR"):

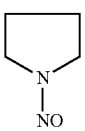

N'-nitrosomethyl-butylnitrosamine ("BMNA"),

N'-nitro-n-butylamine ("NBA") and

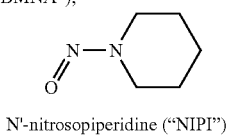

N'-nitrosopiperidine ("NIPI")

Figure 3:
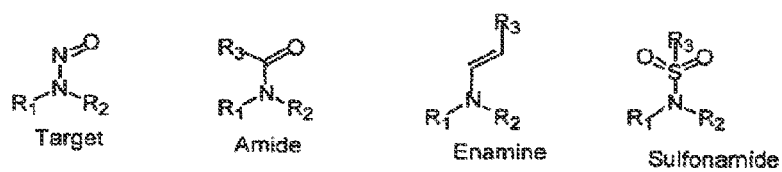
FIG. 3 shows isosteric analougues of nitrosamines.
Figure 4A:
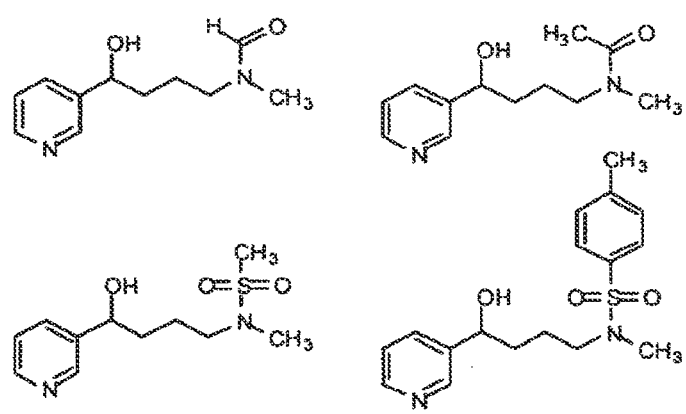
FIG. 4A shows examples of amide and sulfonamide based target analogs.

Possible isosteric analogs for the targeting of nitrosamines are seen in FIG. 3. The molecules shown are all derivatives of the parent amine and can be synthesized in a single step from the secondary amine and corresponding aldehyde or acid chloride. Molecular models of the enamine (FIG. 4A) have shown a good steric complementarily with one of the nitrosamines of interest, NNAL.

Figure 4B:
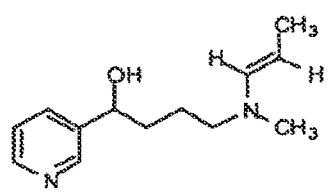
FIG. 4B shows an enamine target analogue (MPAPB) used as a template to prepare a MIP for extraction of NNAL.
Figure 4C:
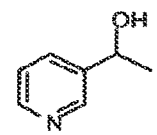
FIG. 4C shows pyridine carbinol used as a template prepare a MIP for extraction of NNAL.

During the design of a suitable template compound for the target analyte NNAL, a particularly interesting template was identified, corresponding to the pyridine carbinol substructure but surprisingly lacking the nitrosamine moiety (FIG. 4B). If sufficient binding affinity and selectivity can be obtained for sub-structural templates, this is the preferred approach. In fact, the binding affinity, selectivity and recoveries obtained with this pyridine carbinol MIP are superior to the MIPs obtained, with the more complex enamine template. Thus, the invention provides a surprisingly effective MIP which comprises a simple template lacking certain key features of the target but providing for effective binding with those target nitrosamines which contain the pyridine-methanol moiety.

Using the functional monomer methacrylic acid (MAA), either of two crosslinkers, ethylene glycol dimethacrylate (EDMA) or trimethylopropane trimethacrylate (TRIM) and either of the two NNAL analogs, 4-(Methylpropenyl-amino)-1-pyridin-3-yl-butan-1-ol (4MPAPB, FIG. 4A) and pyridine carbinol (FIG. 4B) as templates, two different polymers are obtained both exhibiting strong affinity and selectivity for NNAL in organic and aqueous solvent environments.

This invention includes an extraction method for quantitative recovery of the nicotine analog NNAL that entails the steps of preparation of an NNAL-selective MIP in a chromatographic material format, column conditioning, application of a urine sample, removal of interfering compounds and finally selective elution of the NNAL analyte.

By way of explanation and not of limitation, the invention will be further described in more detail with reference to a number of examples. The invention refers to template molecules, polymer materials designed to bind nitrosamines deriving from nicotine and present in organic or aqueous systems, and finally use of said materials in, for example, analytical or preparative separations, in chromatography, for analytical sample pre-treatment and in chemical sensors.

Unless otherwise described, materials are commercially available or can be prepared by conventional techniques. See, for example, B. Sellergren (Ed.) Molecularly-imprinted Polymers: Man made mimics of antibodies and their application in analytical chemistry, part of the series Techniques and Instrumentation in Analytical Chemistry, Elsevier Science, Amsterdam, Netherlands, 2001.

Example 1: Synthesis of Enamine Template (MPAPB)

Anhydrous toluene (freshly dried over sodium) 2 ml was added to a vial containing 4-methylamine-1-(3-pyridyl)-1-butanol (100 mg). 500 mg freshly dried Molecular sieve was added to it. The mixture was stirred for 1 hour under $N_2$. To the mixture 100 µl propionaldehyde was added. The mixture was stirred at 55° C. for 4 hours. The reaction was monitored by HPLC after 1.5 hours. The color of the product was orange-yellow in toluene. The crude product in toluene was directly used for the synthesis of the MIP alter filtration without publication. Template MPAPB yield was around 90%.

Example 2: Synthesis of MIP Using Pyridine Carbinol as Template

To pyridine methanol (97 µl) 3.74 ml of purified TRIM (purified over basic alumina), functional monomer MAA (1020 µl), porogenic solvent toluene (7.1 ml) and finally initiator ABDV (63 mg) were added and stirred until a clear solution was obtained. The solution was transferred to a glass vial, purged with nitrogen for 5 minutes and flame sealed. Heal induced polymerization was carried out at 45° C. for 24 hours. The polymer mixture was then cured at 70° C. for a further 24 hours.

Processing of the crude MIP material was as follows: the MIP was coarsely crashed and transferred to a Soxhlet thimble. It was excessively washed first with methanol for 12 hours and then with acetic acid for 12 hours in order to remove any remaining template and other non-reacted monomers. After these first extraction steps, the polymer was vacuum dried and then ground and sieved to a line powder within a size range of 20 to 90 μm. As a final extraction step, the finely ground MIP was subjected to a 40 minutes microwave assisted solvent extraction using formic acid as the extraction solution. After drying, the MIP was ready for use.

Example 3: Use of MIPs as Selective Sorbents in SPE

In one embodiment of the invention, the MIP can be packed into solid phase extraction columns for the selective extraction of NNAL from a biological matrix. First, a polypropylene frit was placed in an appropriate SPE column (typically 10 ml capacity for analytical uses), 25 mg of the MIP was then added on top to form a MIP bed and the second frit was firmly pressed onto the surface of the MIP bed. Conditioning of the column was carried out in the following order: 1 ml DCM, 1 ml MeOH and finally 1 ml distilled water were added to the MIPSPE.

The sample, e.g. human urine (5 mL) containing low amounts of the analyte was allowed to pass through the conditioned MIPSPE column. The column was then subjected to vacuum in order to remove the water until the material was dry. Then, polar interfering substances that may have non-specifically associated with the MIP were eluted by a wash with 1 ml distilled water. Again, a drying step using several minutes of vacuum was performed in order to enable the so-called phase-switch (change of the environment from aqueous to organic). At this point, non-polar interfering substances were removed by washes with each 1 ml toluene, toluene:DCM (9:1) and toluene:DCM (4:1). The final selective elution of NNAL was carried out in 3 times elution steps, each of 1 ml DCM.

After solvent evaporation, the samples were reconstituted in the mobile phase and analyzed on an HPLC system: e.g. Merck-Hitachi (L-7000 system) using a beta-basic C18 column, 5 μm, 150×2.1 mm+pre-column 10×2.1 mm. Flow was at 0.25 mL/min, injection volume 100 μL, temperature 30° C. and detection at UV 262 nm. The mobile phase consists of 50 mM NH4PO4 pH 3, 5 mM octanesulfonic acid 20% methanol.

Figure 5A:
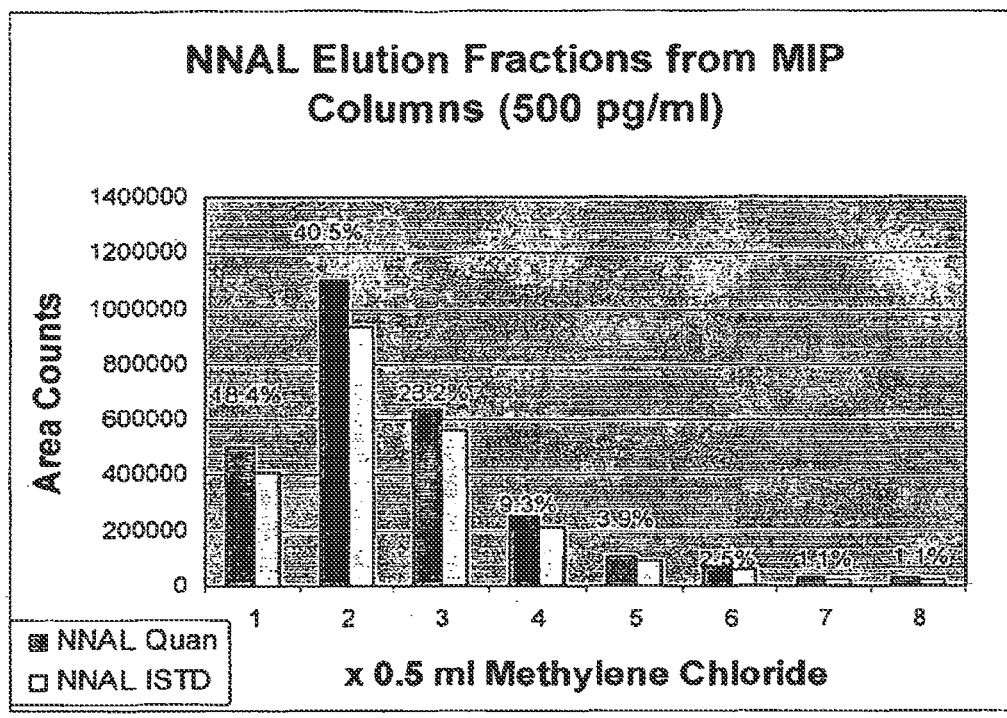
FIGS. 5A and 5B show recovery rates of NNAL using an NNAL-selective MIP.
Figure 5B:
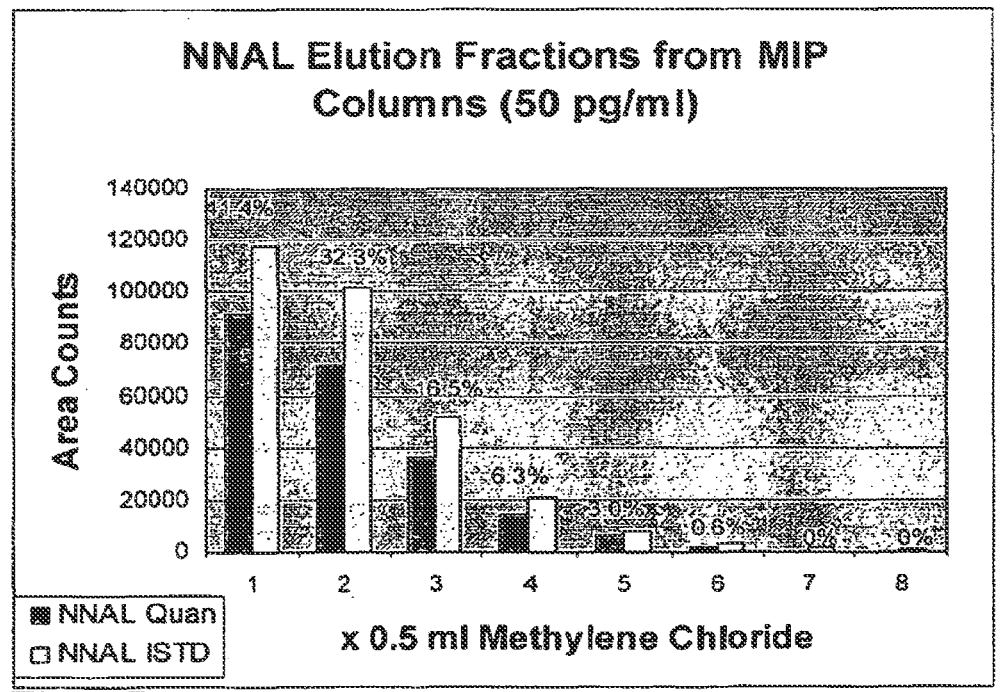
Figure 6:
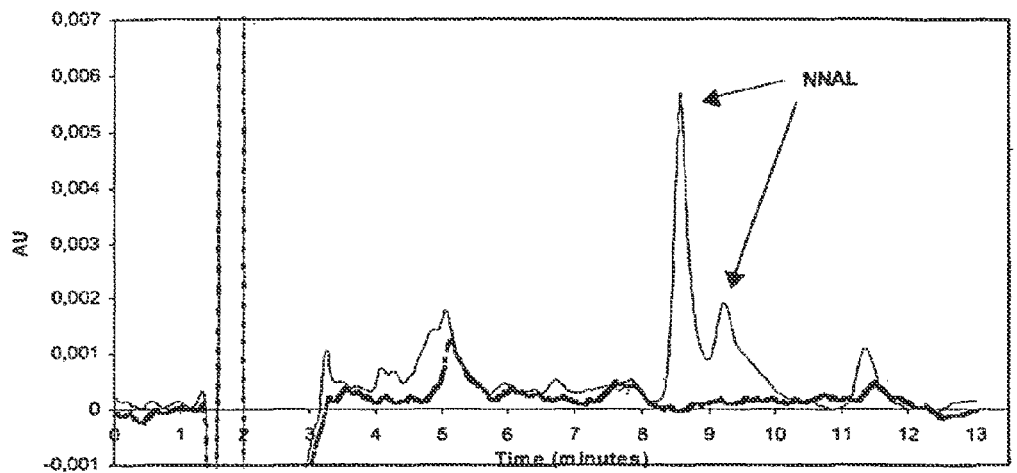
FIG. 6 shows chromatograms obtained after analysis of 1 mL human urine spiked with 0.25 µg NNAL (represented by solid line) and 1 mL blank human urine (represented by bold line)

Under these conditions, NNAL was obtained as a clearly distinguishable double peak eluting at about 8-10 minutes (see FIG. 6, where a 1 ml sample of human urine spiked with 0.25 μg NNAL is compared with NNAL-free urine). The double peak is characteristic for NNAL as it corresponds to its two rotamers. From the structure of NNAL, it can be demonstrated that the side chain on the pyridine ring can have different conformational states. The preferred conformations are called rotamers and for NNAL there are two major conformations. The retention of these two rotamers on an HPLC column will differ. As shown in FIG. 6, the NNAL peak is cleanly separated from interfering substances. It can therefore be easily and accurately quantified. Recovery rates for NNAL (defined as Amount recovered/Amount loaded× 100) are typically up to 90%, depending on the initial levels of NNAL in the biological sample. Recovery rates of close to 100% have been seen with samples containing 50 pg/ml and 500 pg/ml of NNAL (FIGS. 5A and 5B).

Example 4: Use of MIPs as Selective Sorbents in SPE in the Presence of Nicotine Another application of the invention is the use of the MIP as a selective sorbent for NNAL where there are high levels of nicotine present. This illustrates the wide scope of applications of the MIP material and how the selective nature of the MIP can be finetuned for particular samples.

SPE columns were prepared as described in Example 3. Conditioning of the SPE column was carried out in the following order: 1 ml DCM followed by 1 ml MeOH followed by 1 ml 50 mM $(NH_4)H_4PO_4$, pH 4.5. The sample, in this example 5 mL human urine-containing low amounts of the analyte was allowed to pass through the conditioned MIPSPE column. The column was then subjected to a mild vacuum (e.g., 10-80 kPa) to remove water until the material was dry. Polar interfering substances that may have nonspecifically associated with the MIP were eluted by a wash with 1 ml 50 mM $(NH_4)H_2PO_4$, pH 4.5. Another drying step of several minutes of mild vacuum was performed. Further, washes with 1 ml each toluene, toluene:DCM (9:1) and toluene:DCM (4:1) were performed in that order. The final selective elution of NNAL was carried out in 3 elution steps each of 1 ml DCM.

Figure 7:
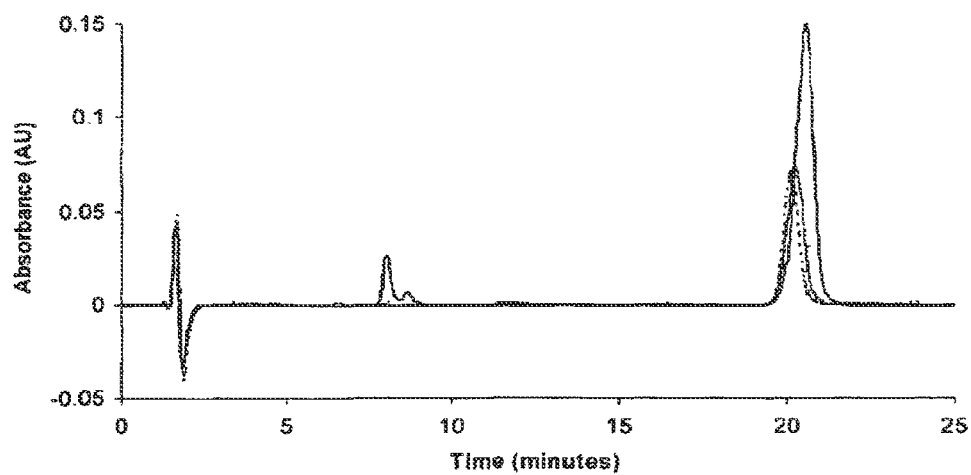
FIG. 7 show an overlay of chromatograms obtained after sample analysis in the presence of nicotine where the solid line represents NNAL and nicotine-spiked sample, dashed line represents eluent collected from loading 1 mL of the NNAL and nicotine-spiked sample, and the long dashed line represents a wash of $(NH_4)H_2PO_4$, pH 4.5.

After solvent evaporation the samples were reconstituted in the mobile phase and analyzed on an HPLC system similar to that described in Example 3. An example chromatogram is shown in FIG. 7, which illustrates how the NNAL is selectively retained on the MIP while the nicotine is removed in the buffer wash.

Example 5: Smoking Articles Incorporating MIPs

Figure 8:
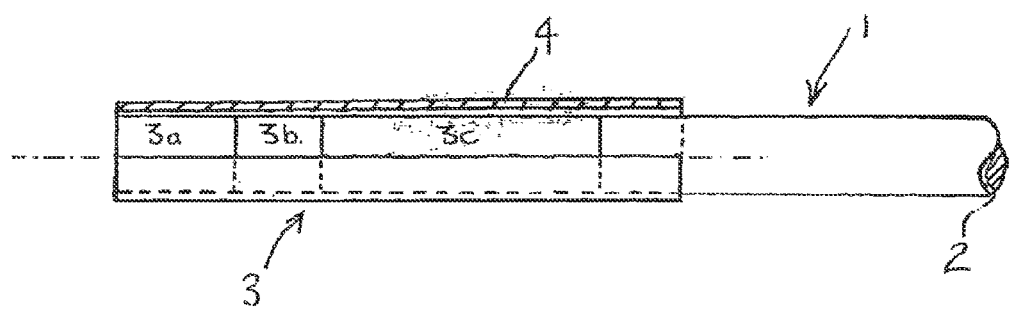
FIG. 8 is a side elevation, partly longitudinal cross-section and partially broken away view of a smoking article with a smoke filter according to the invention.
Figure 9:
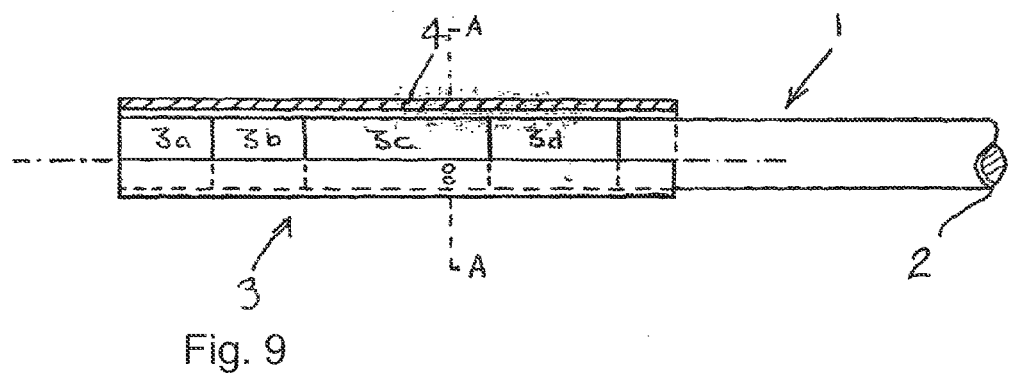
FIG. 9 is a similar view to FIG. 8 of a smoking article with an alternative smoke filter according to the invention.

Referring to the drawings, FIGS. 8 and 9 illustrate smoking articles in the form of cigarettes having a rod 1 of tobacco encased in a wrapper 2 attached to a smoke filter 3 by means of a tipping paper 4. For clarity, the tipping paper 4 is shown spaced from the wrapper 2, but in fact they will lie in close contact.

In FIG. 8, the smoke filter 3 comprises three cylindrical filter elements 3a, 3b, 3c. The first filter element 3a at the mouth end of the filter is 7 mm in length, composed of cellulose acetate tow impregnated with 7% by weight of triacetin plasticizer having a 25 mm water gauge pressure drop over its length. The second filter element 3b, positioned centrally is a cavity 5 mm in length containing 150 mg of activated carbon granules. The third filter element 3c adjacent the rod 1 is 15 mm in length, has a 90 mm water gauge pressure drop over its length, and comprises 80 mg cellulose acetate tow. The tow is impregnated with 4% by weight of triacetin and has 80 mg of MIP specific for volatile nitroamines, produced as described in Example 6 below, distributed evenly throughout its volume in a "Dalmatian" style.

The cigarette shown in FIG. 9 is similar to that of FIG. 8 except that the smoke filter 3 has four coaxial, cylindrical filter elements 3a, 3b, 3c and 3d. The first filter element 3a at the month end of the cigarette is 5 mm in length, and composed of cellulose acetate tow impregnated with 7% by weight of triacetin plasticizer. The second filter element 3b, positioned adjacent the first filter element 3a is a cavity 5 mm in length containing 200 mg of molecularly-imprinted polymer specific for volatile nitrosamines, produced as described in Example 6 below. The third filter element 3c adjacent the second filter element 3b is 10 mm in length and comprises cellulose acetate tow impregnated with 7% by weight of triacetin. The fourth filter element 3d lies between the third filter element 3c, is 7 mm in length and comprises 80 mg of granular activated carbon. A ring of ventilation holes 5 is formed in the tipping paper 4 in a radial plane A-A which deliver air into the third filter element 3c about 3 mm downstream of the junction with the fourth filter 5 element 3d when smoke is inhaled through the cigarette.

The following Examples further illustrative this aspect of the invention.

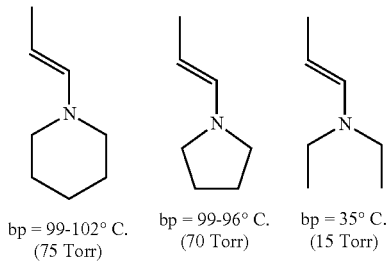

bp = 99-102° C. (75 Torr)   bp = 99-96° C. (70 Torr)   bp = 35° C. (15 Torr)

Figure 10:
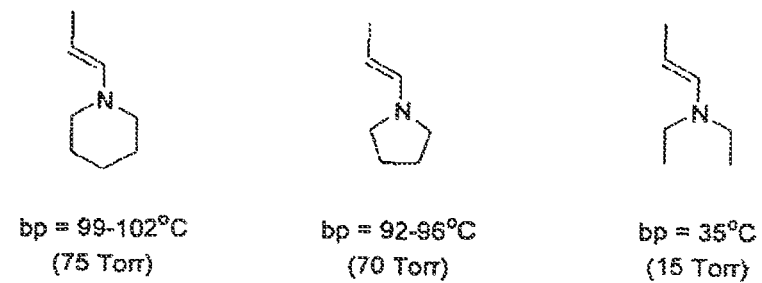
FIG. 10 shows the chemical structure and boiling point for three products described in Example 6.

Two equivalents of an appropriate secondary amine, e.g. dimethylamine, diethyl amine, pyrrolidine, piperidine or morpholine, are dissolved in anhydrous ether and freshly dried molecular sieves (50 g/mole amine) are added. The mixture is then cooled to −5° C. and stirred. One equivalent of propionaldehyde is then added drop-wise to the cooled mixture, maintaining the temperature at 0±5° C. The mixture is allowed to stand in a cold bath overnight and is then filtered. The product is obtained in approximately 50% yield by distillation of the filtrate under reduced pressure, depending on the boiling point of the product. By way of example, structures and boiling points are shown in FIG. 10. (See, Brannock, et. al., J. Org. Chem., 1964, 29, 801-812.)

By using a strong acid functional monomer, the enamine is protonated, thus creating the necessary non-covalent interaction during the imprinting step. The positive charge resides on the carbon atom attached to the nitrogen, a structure stabilized due to derealization to give an iminium ion. This positions the acidic functional monomers correctly for later recognition of volatile nitrosamines. As there is no opportunity to delocalise the positive charge, protonation of the enamine nitrogen is disfavored. (See, Cook, et al., J. Org. Chem., 1995, 60, 3169-3171.)

It may be preferred to use a more strongly-acidic functional monomer than MAA. Further 5 embodiments incorporate 4-vinylbenzoic acid or 4-vinyl benzene sulphonic acid as functional monomers.

Example 7: Synthesis of a MIP Using an Enamine as Template

A pre-polymerization solution is prepared by dissolving the desired enamine (1 mmol), an acidic functional monomer (4 mmol), a cross-linking monomer (20 mmol) and a free-radical initiator (1% w/w total monomers) in a appropriate porogenic solvent. The functional monomer is either MAA or trifluoromethacrylic acid (TFMAA), the cross-linker is either EDMA or TRIM, the free-radical initiator is ABDV and the porogenic solvent is one of chloroform, toluene, acetonitrile or acetonitrile/toluene (1/1 v/v). The solution is transferred to a polymerization vessel, cooled to 0° C. and then purged with $N_2$ for 5 minutes, after which the vessel is flame sealed. Polymerization is initiated at 45° C. and allowed to continue at this temperature for 24 hours. The polymer is then cured at 70° C. for a further 24 hours.

The crude MIP material is then processed. The MIP is coarsely crushed and transferred to a Soxhlet thimble. It is then extensively extracted (i) with methanol for 12 hours and (ii) with acetic acid for 12 hours, in order to remove the template molecule and any unreacted monomers. After these first extraction steps, the polymer is vacuum dried, ground, and sieved to give particles of the desired size range, e.g. 25-36 µm. The finely-ground MIP is then subjected to a final extraction step, involving 40 minutes microwave assisted extraction using formic acid as the extraction solvent. The MIP is then dried in vacuo for 24 hours.

Figure 11:
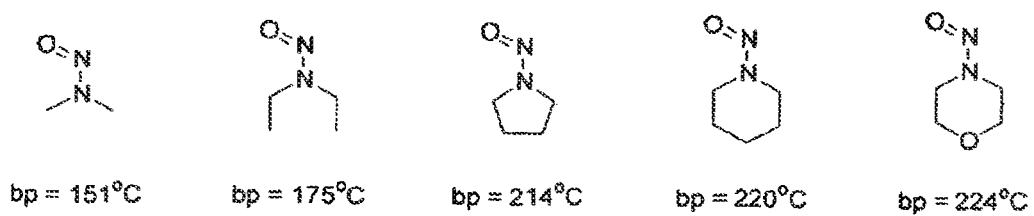
FIG. 11 shows the chemical structure and boiling point for select volatile nitrosamines.

Alternatively, the target TSNA may be used in place of the enamine. The boiling points of select volatile nitrosamines at normal atmospheric pressure are shown in FIG. 11.

Example 8: Use of the MIP Material of Example 2 and/or Example 7 in the Treatment of Tobacco Extracts The polymer produced in accordance with the method of Example 2 or Example 7 is incorporated into a solid phase extraction column, and the column is conditioned by passing through dichloromethane (DCM), methanol and finally distilled water.

Shredded Burley tobacco leaf is extracted with water for 15 minutes at 60° C. The tobacco is separated from the solution by filtration and dried. The solution is passed through the column and allowed to adsorb TSNA from the extract. The column is then drained and the solution concentrated by film evaporation, the concentrate is then recombined with the extracted tobacco and dried in air.

TSNA adsorbed by the polymer can be eluted from the column using DCM.

Example 9: Use of the MIP Material of Example 2 or Example 7 in the Treatment of Tobacco Extracts Flue-cured shredded tobacco leaf is extracted with water for 15 minutes at 60° C. The tobacco is separated from the solution by filtration and dried. The solution is mixed with the MIP of Example 2 or Example 7, during which period the polymer adsorbs the TSNAs selectively from the solution. The MIP is then mechanically separated from the extract by filtration or by centrifugation. The solution is concentrated by evaporation; the concentrate is then recombined with the extracted tobacco and dried in air.

The MIP can be regenerated by elution with DCM, methanol and finally deionised water or pH 4 buffer, for reuse.

Example 10: Use of the MIP Material of Example 2 or Example 7 in the Treatment of Tobacco Extracts Using a continuous extraction process, US Blend-type shredded tobacco leaf is loaded into a first extraction chamber into which super-critical carbon dioxide is fed. After contacting the tobacco, the carbon dioxide is fed into a second extraction chamber containing a MIP produced as described in Example 2 or Example 7. Having contacted the polymer, the carbon dioxide is returned to the first extraction chamber and contacted again with the tobacco. The cyclic process is continued until the TSNA content of the tobacco has been reduced to a desired level, whereupon the carbon dioxide is vented from the system, and the tobacco removed from the first chamber. The MIP in the second chamber is then regenerated using DCM, methanol and acetic acid.

Example 11: Use of the Molecularly-Imprinted Polymer Material Developed for 4-methylnitrosoamino-1-(3-pyridyl)-1-butanol (NNAL), in the Treatment of an NNAL and Nicotine Containing Solution The polymer produced in accordance with the method of Example 2 was incorporated into a solid phase extraction column, and the column was conditioned by passing through phosphate buffer solution.

Aqueous standard solutions of NNAL and nicotine were prepared in phosphate buffers over the pH range 3.0-7.5. The buffered standard solution was passed through the column, this fraction was collected and analyzed for NNAL and nicotine content. A buffered wash solution was passed through the column, this fraction was also collected and analyzed for NNAL and nicotine content.

The solutions were analyzed by HPLC with UV detection. Optimum conditions for the MIP to retain NNAL and recover nicotine are observed at the pH range 4.0-4.5. At lower pH values the nicotine is protonated and has little interaction with the polymer, so is carried through with the aqueous buffer.

Example 12: Use of the MIP material developed for 4-methylnitrosoamino-1-(3-pyridyl)-1-butanol (NNAL), in the Treatment of a NNAL and TSNA Containing Solution The polymer produced in accordance with the method of Example 2 is incorporated into a solid phase extraction column, and the column was conditioned by passing through dichloromethane (DCM), methanol and finally distilled water.

Aqueous standard solutions of NNAL and TSNAs (NAB, NAT, NNK and NNN) were acidified with glacial acetic acid to pH 3. The standard solution was passed through the column, followed by three glacial acetic acid solution washes. This fraction was analyzed for NNAL and TSNA content by GC-TEA. Three washes of dichloromethane were passed through the column, this fraction was also analyzed for NNAL and TSNA content.

The MIP retained 91% of the NNAL, 65% of the NNK and an efficiency of about 20-30% for the other (less structurally similar) TSNAs.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

The invention claimed is:

1. A molecularly imprinted polymer selective for at least one tobacco-specific nitrosamine, wherein said molecularly imprinted polymer is obtained using a functional or structural analogue of a tobacco-specific nitrosamine as a template, and includes an imprint of the functional or structural analogue of a tobacco-specific nitrosamine.

2. The molecularly imprinted polymer according to claim 1, wherein said at least one tobacco-specific nitrosamine is derived from nicotine, nornicotine, anabasine or anatabine.

3. The molecularly imprinted polymer according to claim 1, selective for the nicotine-derived nitrosamine NNAL.

4. The molecularly imprinted polymer according to claim 1, wherein the polymer has been prepared using an isosteric analogue of a tobacco-specific nitrosamine as a template.

5. The molecularly imprinted polymer according to claim 1, wherein the polymer has been prepared using 4-(methyl-propenyl-amino)-1-pyridin-3-yl-butan-1-ol as a template.

6. The molecularly imprinted polymer according to claim 1, wherein the polymer has been prepared using pyridine carbinol as a template.

7. The molecularly imprinted polymer according to claim 1, wherein the polymer has been prepared using a compound that includes a substructure of the tobacco specific nitrosamine.

8. A kit, comprising:
the molecularly imprinted polymer according to claim 1; and
instructions for using the molecularly imprinted polymer to perform at least one of detecting, quantifying, and separating nitrosamines in a sample.

9. A smoking article, comprising:
a smoking material; and
the molecularly imprinted polymer according to claim 1, selective for at least one tobacco-specific nitrosamine found in the thermall decomposition products of the smoking material.

10. The smoking article according to claim 9, wherein the molecularly imprinted polymer is selective for at least one volatile nitrosamine found in the vapor phase of the thermal decomposition products of the smoking material.

11. A smoke filter, comprising: filter material;
and the molecularly imprinted polymer according to claim 1.

12. The smoke filter according to claim 11, wherein the molecularly imprinted polymer is selective for at least one volatile nitrosamine found in the vapor phase of the thermal decomposition products of tobacco or a tobacco substitute.

* * * * *